United States Patent [19]

Cosman

[11] 4,378,809

[45] * Apr. 5, 1983

[54] AUDIO-TELEMETRIC PRESSURE SENSING SYSTEMS AND METHODS

[76] Inventor: Eric R. Cosman, Belmont, Mass. 02178

[*] Notice: The portion of the term of this patent subsequent to Oct. 10, 1997, has been disclaimed.

[21] Appl. No.: 161,098

[22] Filed: Jun. 19, 1980

Related U.S. Application Data

[63] Continuation-in-part of Ser. No. 895,953, Apr. 13, 1978, Pat. No. 4,281,666, and Ser. No. 895,954, Apr. 13, 1978, Pat. No. 4,281,667, and Ser. No. 908,615, Jun. 12, 1981, abandoned.

[51] Int. Cl.³ ............................................. A61B 5/00
[52] U.S. Cl. ................................ 128/748; 128/675; 73/701; 73/717
[58] Field of Search .................. 128/748, 675; 73/701, 73/702, 716, 717

[56] References Cited

U.S. PATENT DOCUMENTS

4,014,319  3/1977  Favre .................................. 128/748
4,206,761  6/1980  Cosman .............................. 128/660

*Primary Examiner*—Kyle L. Howell
*Assistant Examiner*—John C. Hanley
*Attorney, Agent, or Firm*—Richard J. Birch

[57] ABSTRACT

A differential pressure sensing device is fully implanted beneath the skin in the living body such that its pressure responsive means, such as a diaphragm means, senses the difference in pressure between an internal bodily pressure and the pressure on the skin which is just above the sensor. The sensor has a stop, or a mechanical contact means, for the diaphragm means so that the diaphragm will be pressed against the stop when an externally applied pressure on the skin equals or exceeds the internal pressure. The sensor also has a means with a detectable parameter that can be detected outside the body by external apparatus. The external apparatus also converts the parameter to an audible sound or audio signal. The parameter has a specific response when the diaphragm is near the stop position, and this response can be heard via the audio signal. Thus by increasing the externally applied pressure to the skin above the sensor and listening for the characteristic audio signal corresponding to the diaphragm being at or near the stop position, one can determine the external pressure needed to balance the internal bodily pressure, and thus measure the latter.

10 Claims, 5 Drawing Figures

AUDIO-TELEMETRIC PRESSURE SENSING SYSTEMS AND METHODS

CROSS REFERENCES TO RELATED APPLICATIONS

The present application is a continuation-in-part of my co-pending applications; Ser. Nos. 895,953, Apr. 13, 1978, now U.S. Pat. No. 4,281,666, 895,954, Apr. 13, 1978 now U.S. Pat. No. 4,281,667, and 908,615, June 12, 1981, abd., which in turn derive from my original applications, Ser. Nos. 697,951 and 697,952 both filed on June 21, 1976 both abd.

BACKGROUND OF THE INVENTION

In these co-pending applications, in vivo telemetric pressure sensing devices, systems and methods were described for which the sensor, once implanted in the body, could be interrogated telemetrically by means of any of a variety of physical principles, and it could be calibrated in vivo by pressing on the skin above the sensor so as to drive the sensor's diaphragm means or associated movable elements against a stop within the sensor, as indicated by a telemetric signal or response of the device at or near the stop position. Further, by pressing on the skin with a pressure cuff or force applicator until the stop position was achieved, which corresponds to a balance of pressure across the sensor, the internal pressure could be measured without need for a calibration of the sensor prior to implantation. Thus, the approach is one where no wires or tubes need to penetrate the skin, and one can get an accurate pressure reading by calibrating the device in vivo using a null pressure or pressure balancing method across the intact skin. As stated in my several papers on the subject, including: A Pressure-Balanced Radio Telemetry System for the Measurement of Intracranial Pressure, J. Neurosurgery 47 899–911 (1977), and, A Telemetric Pressure Sensor for Ventricular Shunt Systems, Surg. Neurol. 11, 287–294 (1979), the method is the analog of measuring blood pressure by the sphygmomanometric method, except that an implanted pressure sensing device is used in the former in place of the natural arteries in the latter.

My previous applications stated that there are a multitude of ways of telemetrically detecting that the sensor's movable diaphragm or cooperatively connected movable elements are at or near their stop or balanced position: "This equilibrium condition or balanced position of the movable element is detected with an external detection system by means of electromagnetic, acoustic, radiation, mechanical, or other methods of coupling across the skin to the implanted sensor"; and, "A displacement of 6 (movable element) relative to 5 (a relatively fixed portion of the sensor) can be made to cause changes in some physical, electrical, or magnetic characteristic of the sensor." Some specific examples of the changeable detectable characteristic or detectable parameter were given including the resonant frequency of an electrical circuit, movements of the diaphragm means or associated movable elements to be detected by acoustic, ultrasonic, echo-reflection, doppler shift or other scattering means. However, it was stated that these diverse means of telemetric detection and diverse types of physical characteristics are subsumed under the general concept of the invention approach, namely of seeking a balance condition of the sensor and applying a variable, known external pressure to the intact skin over the sensor and simultaneously detecting the occurrence of the balance condition by one of a diverse number of telemetric means as one varies the external pressure through the balance condition.

In this continuation-in-part application, several other examples of specific telemetric detection means, specific aspects of the associated external detection apparatus and specific means of the implanted sensor having a detectable parameter or detectable characteristic are described in more detail. In particular, acoustic coupling of the detection apparatus, to the implanted sensor means of producing an acoustic response of the implanted sensor at or near the balance position or stop position of the diaphragm means, and means of converting a non-acoustic characteristic response parameter of the implanted sensor to an acoustic response through apparatus cooperatively connected to the external detection apparatus will be described. Associated inventions will then be claimed. The production of an acoustic signal or response to indicate, to the person measuring the pressure, that the balance condition of the implanted sensor has been reached, as he is simultaneously varying the cuff pressure so as to search for the balanced pressure condition, makes the analogy of the pressure-balanced telemetric method of the previous application even closer to that of convention, time-tested sphygmomanometric blood pressure measurements. In the latter, in its simplest form, a stethoscope is held on the skin near a pulsating blood artery, and a pressure cuff is inflated on the skin to gradually occlude the artery. This is analogous to driving the implanted sensor to its stop position. One listens to the artery pulsations until they stop, at which point the cuff pressure equals the maximum blood pressure, which is visualized on the cuff's pressure guage in the pressure balanced telemetric method, by similarly converting the implanted pressure sensor's response characteristic at the balance point to an audible acoustic response, one frees the operator from having to watch a visual indicator of the balance condition, and he can merely watch the cuff pressure gauge. This can be an aid and a convenience in making the measurement, and there are diverse ways of implementing the acoustic, telemetric, pressure-balancing method as will be illustrated in several examples below.

The following is a listing of the Figures used to illustrate specific examples of the general concept of the invention of audio-monitored, telemetric, pressure balanced, in-vivo pressure measurement.

The numbers on the figures are analogous to the numbering on figures in the above-mentioned related patent applications.

Figure 1:
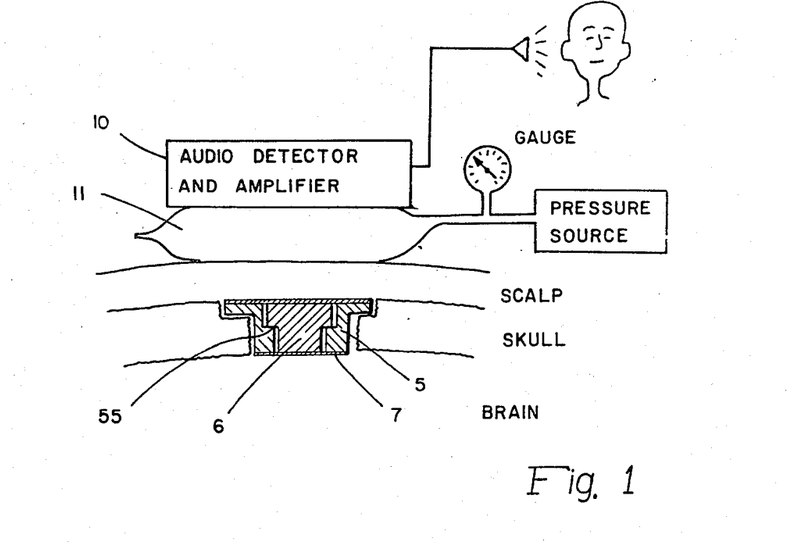
FIG. 1 shows a simple system of listening directly to an implanted two-diaphragm sensor with a stethoscopic device.

Referring to FIG. 1, a two diaphragm pressure sensor is implanted in the skull, and we will therefore, in this special case, be illustrating the measurement of intracranial pressure, P (ICP). The brain pressure P (ICP) acts on inner diaphragm 7 which is coupled by piston 6 to upper diaphragm 7', which, in turn, is in mechanical pressure, communication with the scalp above it. We mean by mechanical pressure communication of 7' with the skin above it that any pressure; P (EXT) applied to the exterior of the skin above the sensor such as atmospheric pressure (if nothing is touching the skin from outside the body), or external pressure from a cuff applied on the skin, or a finger pressing on the skin, or a force applicator such as a plunger or diaphragm applied to the skin; will be felt by the diaphragm 7'. Usually 7' is actually facing and in contact with the inner surface of the skin, but if the sensor is adapted to have a gap between it and the skin, then bodily tissue or fluid will eventually fill the gap to supply the communication.

The coupling element 6 has a shoulder on it which stops against the stop 55 on the housing 5 when the pressure P (ICP) is equal to or exceeded by the pressure from above on 7'. Actually the stop could be made to correspond to any known relationship between P (EXT) and P (ICP), but the balance condition, P (EXT)=P (ICP, is the most convenient for this illustration. When P (ICP exceeds P (EXT), P (ICP)>P (EXT), then the element 6 will lift off the stop 55. The pressure balancing telemetric principle involves varying the known P (EXT) in such a way as to achieve a balance of P (ICP) and P (EXT), and to simultaneously detect some detectable characteristic response or detectable characteristic parameter of the sensor when 6 is at the stop position by means of an external detection apparatus which is interrogating the sensor, so that one in fact knows that the element 6 is near or against stop 55, at which point P (EXT)=P (ICP). In FIG. 1 the means of detecting condition that element 6 is near or against the stop 55 is derived from the fact that P (ICP) has a physiologic modulation caused by the cardiac related pressure pulsations which are characteristic of a living body. As pointed out in my previous related patent applications and in the references cited above, cardiac related pulsations are very useful in determining that the pressure sensor is really working properly, and they are ever-present in internal bodily pressures. We can use this fact in the illustration of FIG. 1 to aid in detecting that the movable element 6 is against stop 55 as follows: an external acoustic detector 10 is placed (near) or against the skin above the sensor and detects the acoustic signals caused by the pulsating displacements of diaphragm 7 and 7' and element 6. A stethoscope may serve for detector 10, since this device converts the acoustic impulses from the sensor's pulsating diaphragm directly into audible acoustic signals by means of its intrinsic acoustic amplification qualities. This acoustic sensing method is well known in blood pressure measurements where the pulsating radial motion of arteries is detected by a stethoscope. Thus, as pressure P (EXT applied by the cuff 11 to the skin is increased, the element 6 will be driven to stop 55, at which point the cardiac related acoustic pulses will begin to cease, and the measurer will know that the stop has been reached, and thus that P (EXT)=P (ICP).

Thus, FIG. 1 illustrates a characteristic response parameter of the sensor when it is implanted in a living body, namely the amplitude or frequency of acoustic pulsating waves, which changes as the stop position is reached, i.e., goes from pulsating to non-pulsation, and thereby indicates that the balance point has been reached.

The acoustic radiation from the mere motion of the diaphragms and element 6, as cited above, is not the only response parameter of a sensor like that of FIG. 1 which will allow acoustic knowledge that the stop position has been reached. The element 6 and the stop 55, if made of relatively hard material will produce an acoustic sound when they strike each other, and this sound can be heard with a stethoscope. For example, as the pulsating element 6, pulsating from the intrinsic pulsation of P (ICP), approaches the stop 55, then it will tap against the stop causing a tapping sound of cardiac (heart beat) frequency. This, too, would be a characteristic response parameter of the sensor that could be converted to an audible signal by the stethoscope. In this case, one would, for example, increase P (EXT) until the tapping begins, i.e. 6 is near stop 55, and continue to increase P (EXT) until the tapping stops, i.e. 6 is pinned against stop 55. Between those limits of P (EXT), P (EXT)=P (ICP). Note that P (EXT) is read out on a pressure gauge in FIG. 1. Also the cuff is under the stethoscope, but it could also be above it.

FIG. 1 shows the close relation between the method of my previous applications and the well known sphygmomanometric blood pressure measuring method. This application draws the relation closer by invoking the stethoscope as the acoustic telemetric interrogator of the implanted pressure sensor. The living body's cardiac pressure variations on P (EXT) are made use of in the above description to aid in the acoustic detection of the stop position, but the acoustic method is not restricted by these natural and pervasive in-vivo pulsations. As will be shown below, external modulations of P (EXT) or other types of externally applied oscillatory forces applied to the sensors moving pressure responsive elements could also serve to produce such acoustic responses associated with the stop position as described above.

Figure 2:
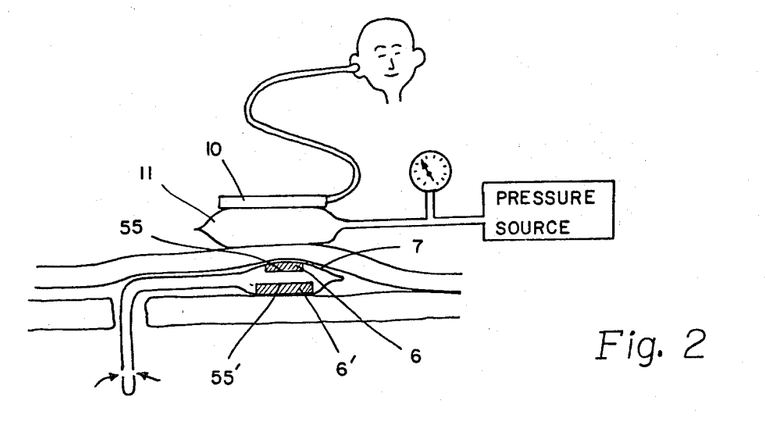
FIG. 2 is similar to FIG. 1, but uses an implanted sensor with only a single flexible diaphragm.

FIG. 2 shows a totally different geometry of implanted sensor to illustrate that a wide latitude is possible in the sensor to still achieve the acoustic specialization of the telemetric balancing method claimed in my previous application. The sensor in FIG. 2 senses an internal bodily fluid pressure, in this case CSF, or cerebrospinal fluid, in the brain. The fluid is conduited to the sensor by a tube 29. The sensor here comprises a housing which defines a chamber therein, at least a portion of the housing walls, and possibly all of the housing, is flexible. Thus the chamber walls 7 themselves serve as the movable pressure responsive element. The fluid pressure inside the chamber, P (ICP), tends to push the wall 7 outward, and the external pressure of cuff 11, P (EXT), on the skin above the sensor, tends to collapse it. Changes in the difference of these opposing pressures cause the movable portion of the walls 7 to move. In particular cardiac modulations of P (ICP) or modulation of P (EXT) will again cause a pulsation of the housing wall 7 which can be detected by an acoustic detector and amplified to an audible or hearable level. In addition, or alternatively, elements 6 and 6' are also shown attached to the flexible wall 7 with both their inward-facing surfaces 55 and 55', constituting what we can call stops, so that when 7 is depressed by an increasing P (EXT), until P (EXT) is about equal to P (ICP), then 55 will begin to contact 55', causing a diminishing amplitude to the diaphragm pulsations as well as the onset of a tapping sound, which also can be heard. As P (EXT) is further increased, all sound will cease when 6 is fully pinned against 6'. Note that 6 and 6' can be chosen to be of metal or hard plastic to improve the sonic response when they strike each other, and they may be shaped in a variety of ways to do the same. One or both may comprise a magnetic material so that physical vibration of 6 or 6' may be achieved by an oscillating, variable, or impulsive magnetic or electromagnetic field impressed upon them from a source outside the body. This may also serve to produce a tapping sound at the balance or stop point, or it may be used to merely produce the physical movement response which is detected acoustically, the cessation of which signals the achievement of the balance or stop position.

Figure 3:
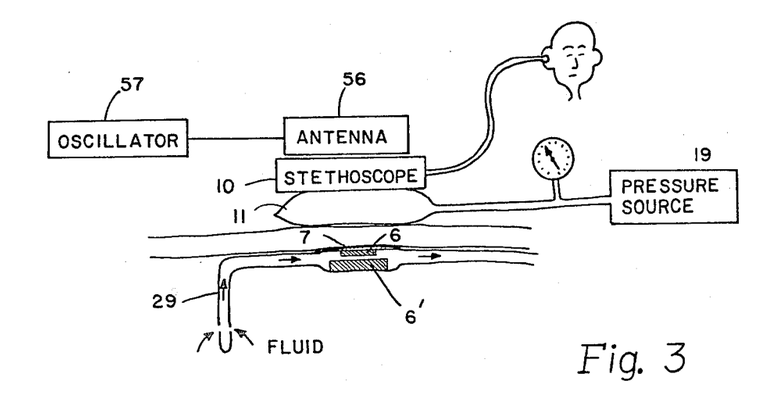
FIG. 3 is similar to FIG. 2 except that an oscillating magnetic force on the diaphragm helps determine the pressure-balance condition of the sensor.

This last situation is depicted in FIG. 3, wherein an external oscillating magnet field is emitted from the field antenna 56 which is powered by the associated driving oscillator 57. The field produces a magnetic force on element 6 which makes it vibrate or move in accordance with the time dependence of the external field. When P (EXT) approaches P (ICP), element 6 will then strike element 6', and the sound will be picked up by the stethoscope or other sonic detector. Other means of impressing a modulating or impulsive, time-dependent force on the sensor's movable elements are possible. For example, if 6 is a conductive element, or coil, or conductive loop, then an impulse electromagnetic field from an external apparatus can cause inductive forces on 6 which can also produce a motion. Again, when this more rapid force is superposed on top of the more slowly varying cuff pressure P (EXT), then it may serve to signal the approach to the stop position of the sensor's movable elements as described above. Other mechanical means to achieve the modulating internal force on the sensor's movable element, such as acoustic, mechanical, vibratory, or modulated pressure sources, may also be employed for this purpose. An illustration of the last type is shown in the next figure.

Figure 4:
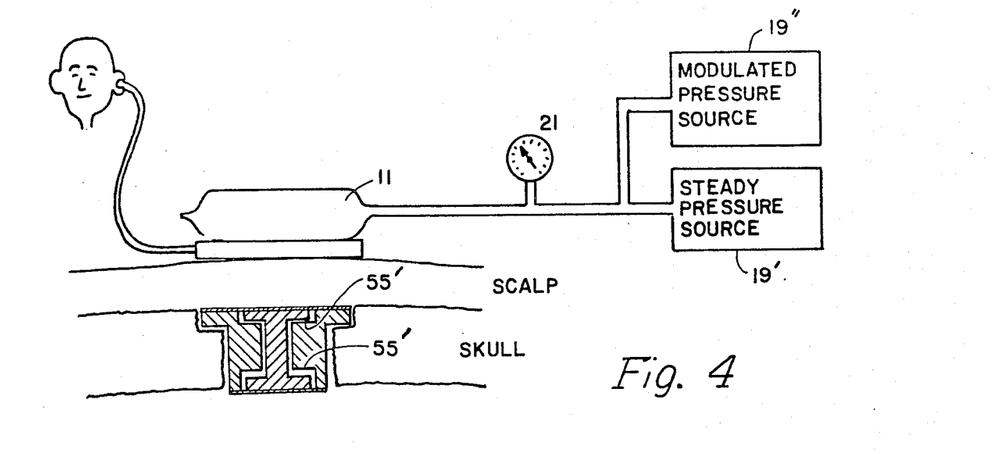
FIG. 4 is similar to FIG. 3 except a modulating applied pressure replaces the modulating magnetic force.

FIG. 4 shows a scheme similar to those just described, except for the addition of a more rapidly varying modulating pressure $\Delta P$ (EXT) being superposed on the more slowly varying external pressure P (EXT). Pressure $\Delta P$ (EXT) may be generated by another pressure source apparatus 19" which is coupled into the pressure cuff along with the more smoothly varying pressure source 19' for P (EXT). The pressure source for P (EXT) may be static, and the slower variations in P (EXT) may merely be achieved by the operator himself pressing the cuff harder or less hard against the patient's scalp. The nature of the time-dependence of $\Delta P$ (EXT), or of the electromagnetic modulating force of the above examples, may vary widely, from sinusoidal variations to descrete impulses or other functions of time, and their amplitudes may be adjustable depending on the situation, i.e., value of P (ICP), distance from implant, orientation, etc. It is noted that mere finger pressure or tapping on the skin above the sensor is a simple but possible means of producing this modulation.

Another aspect of FIG. 4 is notable. In addition to the stop 55 of piston 6 against, in this case, housing body 5, which stops the motion of piston 6 at say the balance point when P (EXT) exceeds P (ICP), there is also a second stop 55' of piston 6 in its upward movement. Stop 55' may correspond to a given relationship of P (ICP) to P (EXT) in the domain where P (ICP) exceeds P (EXT), or it may merely be a prescribe displacement of piston 6 from the balance stop position 55. In any case, it may be arranged that piston 6 is pinned against 55' for large enough P (ICP), and piston 6 may only be free to to move between 55 and 55' if P (ICP) and P (EXP) differ by less than some specified amount. In such a case, the cardiac pulsation of P (ICP) or, alternatively, some externally applied modulating-force on the sensors movable element, will cause the piston to "rattle" between 55 and 55' as P (EXT) approaches P (ICP), and this can be another way of producing the sonic signal at the balance point.

In the examples so far, a variety of ways of producing a direct acoustic response characteristic of the implanted pressure sensor, in accordance with the general principles of my previously mentioned patent applications, have been shown, and this sonic output of the sensor itself serves to identify a predetermined differential pressure condition across the sensor's pressure responsive element to enable in-vivo calibration of the sensor and actual pressure measurement itself. Alternatively, the sensor can be adapted to produce some other kind of response characteristic at, or near its stop position, or arising from its displacement from the stop position, or arising from velocity, accelerator, or some other parameter of its motion, such that its response characteristic can be detected by appropriate external apparatus outside the body. The external apparatus can, in turn, convert the detected response characteristic to an audible acoustic signal that can be heard by the operator as the pressure-balancing or other in-vivo calibration (such as finger pressure on the skin above the sensor) is performed. As cited in my original patent applications, the nature of the sensor's detectable response characteristic or response parameter can be based on a wide variety of physical principles or behavior of the sensor's movable element and cooperatively associated components. For example, the detectable characteristic or response may be derived from means involving mechanical principles electromagnetic principles, electronic circuitry, radiation scattering or absorption, interferometry, mechanical resonance, electrical resonance, nuclear radiation sources and absorbers, ultrasonic scattering or absorption, etc. which enable the characteristic or response to be detected by related telemetry means to traverse the intact skin above the sensor. The detected characteristic response or parameter may be converted to audible acoustic signals so as to produce a value, level or variation of the amplitude, frequency or phase of the acoustic signal, whereby the state of displacement, distortion, motion or position (relative to the stop reference position) of the sensor's movable element or elements may be determined by operator's listening to the acoustic signal.

Figure 5:
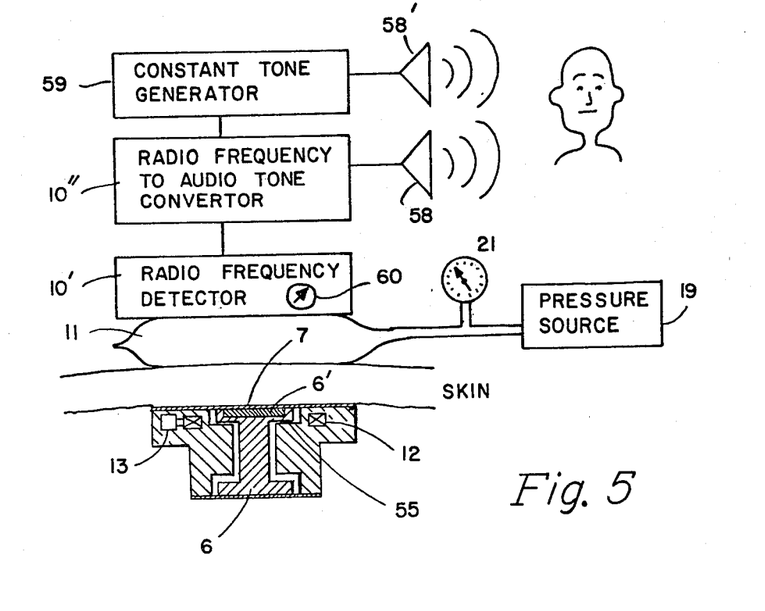
FIG. 5 illustrates a system where the implanted sensor has a resonant circuit in it, the frequency of which is converted to an audio tone outside the body.

FIG. 5 illustrates an example of the above audioconversion method. The implanted sensor has built into it a resonant electronic circuit, in this case involving a parallel coil 12, and capacitor 13. The diaphragm 7 has connected to it a tuning element 6', which is part of the movable element that stops against stop 55. As the diaphragm 7 moves, the tuning element changes either the inductance of coil 12 or the capacitance of capacitor 13, and thus changes the resonant frequency of the circuit. The resonant radio frequency of the implant is detected by a frequency swept radio frequency oscillator, antenna, and related circuitry 10' of the grid-dip type outside the body. Thus, the implant's radio frequency is an analog indicator of the position and motion of the diaphragm and the movable elements 6 and 6'. When 6 is driven against stop 55 by external cuff pressure P (EXT), then the corresponding balance frequency $f_o$ can be determined in-vivo after implantation; i.e., the implant can be zero-calibrated in-vivo. Also, the so-determined value of $f_o$ enables the bodily pressure P (ICP) to be measured, since when P (EXT) is varied until $f_o$ is detected, then, one knows that P (EXT) has approached P (ICP). To make such a measurement of P (ICP), one would usually need to be visibly cognizant of two visible indicators; the position of the meter or chart recorder displaying the implant's resonant radio frequency, and the position of the pressure gauge displaying the cuff pressure P (EXT). As with blood pressure sphygmomanometry, it would be very convenient to free the operator of having to see one of these visual inputs, and instead, hear it. This can be done, for example in the present example, by converting the analog signal which is a representation of the implant's resonant frequency to an audio signal representation. For instance the external apparatus might produce a voltage as a function of resonant radio frequency which would ordinarily drive a meter, but could be sent through a voltage-to-frequency converter to produce an audio frequency which is proportional to the resonant radio-frequency of the implant. This audio frequency could then drive a speaker 58 to produce a variable audio tone. The operator could then literally hear the position and movement of the implant's movable elements. Now one would need only look at the cuff pressure gauge and simultaneously listen for the audio tone end point corresponding to the stop position of the pressure sensor. One can, as in the examples of FIGS. 1, 2, 3, and 4, hear the cardiac modulations and cessation thereof when the stop position is reached. One can, upon monotonically increasing or decreasing P (EXT), listen for the transition from audio tone change to lack of change to indicate that the stop has been reached. It is notable that with regard to frequency response, the human ear is the most sensitive detection organ in the body and, therefore, ideally suited to sensing rates-of-change or, simply, changes of tone as described here. Another feature of the external apparatus in FIG. 5 would be to have, superimposed on the audio signal that eminates from the speaker 58 of the external apparatus, a reference audio tone produced by a tone generator 59 that is coupled to speakers 58'. This reference tone can be made to correspond to the stop position or reference position of the implanted sensor as determined by an in-vivo zero-point calibration maneuver. For example, by having a frequency working point adjustment 60 on the variable frequency oscillator-antenna system 10' that interrogates the implanted sensor for its resonant frequency as in the "grid-dip" technique, one could drive the implant to its stop position by pressing on the skin with one's finger or with an over-pressure of the applied cuff, and then adjust the frequency adjust control so that the audio tone corresponding to the radio frequency of the stop position, $f_o$, equals the above-mentioned reference tone. Subsequently, when pressure balancing with P (EXT) to measure P (ICP), the variable audio tone could be heard to equal the reference audio tone, at which point P (EXT)=P (ICP). The equality of tones is dramatically evident by an audio beat frequency when they are near each other. Because of the extreme sensitivity of the human ear to audio tone changes, minute pressure changes or very fast pressure changes can also be heard, opening up wide diagnostic possibilities. When sensing a fluid pressure, for example in a CSF shunt system, the flow of fluid can, in a sense, be heard as its pulsations and turbulence through the tubes causes small, rapid pressure gradients.

Many variants on the audio-coupled telemetry are possible and are assumed here. In the audio conversion method above, a large variety of other sensor parameters may be used to convert to the audio tone as mentioned above. The parameter may be connected to an audio amplitude, or phase, or some other audio signal such as a clicking sound which equally well may serve as an indicator that the balance point has been reached. If the sensor is essentially a switch, for example having electrical contacts that open or close when the balance point is reached, then an audio tone may merely switch on or off at this point. The external equipment may produce an audio signal which indicates only rate-of-change of pressure, so as to focus attention on cardiac pulsations or other variations. Automatic apparatus may be used to track the pressure signal or audio signal to automatically sense and readout the P (EXT) at the balance point.

It is assumed here that wide latitude in the form and design of the pressure sensor itself is possible. Single diaphragm, double diaphragm, multiple diaphragm, multiply connected diaphragms, bellows, or other pressure responsive means may be used. Rigid housing plus diaphragm means, flexible or semiflexible housings with one or more chambers within may be used. The housing as shown in FIG. 3, may be just a section of flexible tube which is an integral extension of the fluid inlet tube 29. This would be the exact analog of using an artery for blood pressure measurement, except, in a sense, we implant an artificial "artery" for bodily fluid containment. The sensor may have a through-opening or chamber within it, and the diaphragm means may divide it into two chambers to thus measure the difference in pressure between two bodily regions, the audio tone being an indicator of that difference. The stop may or may not be necessary depending if one wants to pressure-balance or in-vivo calibrate, or if one merely wants to hear or detect differential pressure variations, as for example if the sensor is placed in parallel arrangement across a fluid shunt valve to measure gradients across the valve. The nature of the bodily medium, the pressure of which is to be measured, may be tissue or fluid.

The concept of implanting a pressure sensor and telementrically detecting its output or its response and converting that output or response to an audible audio signal opens a new dimension in in-vivo pressure monitoring. In conjunction with pressure-balancing with P (EXT), applied to the intact skin over the sensor, one has a modern analog to the time-tested technique of blood pressure sphygmomanometry. Using the direct sound output of the sensor makes the analogy very close, but also audio conversion technique provides wide latitude in choice of sensor design and response characteristics. It will be appreciated from the foregoing description that the technique can be extended to bodily pressures other than intracranial pressures. Also the technique can be implemented with an implanted sensor that utilizes wires or tubes through the skin.

What I claim and desire to secure by Letters Patent of the United States is:

1. A method for detecting an in-vivo differential pressure, said method comprising the steps of:
   (a) implanting beneath the skin in a living body a differential pressure sensor comprising:
      (1) a flexible-diaphragm means having a first side and a second side, the differential pressure sensor being so adapted that when implanted in the living body the first side of the flexible diaphragm means is in mechanical pressure communication with a first bodily medium and the second side of said flexible diaphragm means is in mechanical pressure communication with a second bodily medium, so that changes in the difference in the pressures in said two bodily regions will cause movement of said flexible diaphragm means;

(2) means located within said differential pressure sensor and at least in part cooperatively connected to said flexible diaphragm means having a detectable characteristic response to movement of said flexible diaphragm means, said detectable characteristic response being detectable by external detection apparatus which is located outside the living body, said external detection apparatus being so adapted to convert said detectable characteristic response to an audible acoustic signal that is an audible representation of the changes in the difference in pressures on said two sides of said flexible diaphragm means;

(b) detecting said audible acoustic signal in order to detect variations in the difference in said two pressures on said flexible diaphragm means and;

(c) applying an external pressure on the skin above said implanted sensor with a controllable pressure source while detecting said audible audio signal, and varying said external pressure on the skin until said audible audio response indicates that said diaphragm means is at a stop position, at which point the value of said external pressure is in a known pressure relationship to said internal bodily pressure to be measured.

2. The method of claim 1 wherein said means having a detectable characteristic response comprises said flexible diaphragm means itself with said detectable characteristic response being the generation of acoustic pressure waves in the bodily media surrounding said pressure sensor when said flexible diaphragm means moves, and wherein said external detection apparatus is a stethoscope, said method further including the step of placing said stethoscope near the living body in which said pressure sensor is implanted in order to detect said acoustic pressure waves with said stethoscope.

3. The method of claim 1 wherein said means having a detectable characteristic response comprises an electronic circuit having an electronic response that is said characteristic response, said method further comprising the steps of detecting said electronic response by transmission of electromagnetic radiation between said pressure sensor and said detection apparatus and converting said electronic response into said audible acoustic signal, whereby the electronic response of said electronic circuit can be detected.

4. A method for measuring an in-vivo pressure, said method comprising the steps of:
(a) implanting in a living body a differential pressure sensor comprising:
(1) a flexible diaphragm means having a first and a second side, said differential pressure sensor being so adapted that when implanted beneath the skin in the living body said first side of said flexible diaphragm means is in mechanical pressure communication with a bodily medium the pressure of which is to be measured and said second side of said flexible diaphragm means is in mechanical pressure communication with an interior portion of the skin, so that changes in the difference in pressure on said two sides of said diaphragm will cause movement of said diaphragm means;

(2) stop means located within said sensor for stopping the movement of said diaphragm means, said stop means thereby defining a stop position of said diaphragm means when the pressure on said second side of said diaphragm means is in a known pressure relationship with respect to the pressure on the first side of said diaphragm means;

(3) means located within said sensor and at least in part cooperatively connected to said diaphragm means having a detectable characteristic response to movement of said diaphragm means;

(b) detecting by means of external detection apparatus located outside the living body, said detectable characteristic response and converting said response to an audible audio signal, whereby said audible audio signal provides an indication that said diaphragm means is at said stop position;

(c) applying an external pressure on the skin above said implanted sensor with a controllable pressure source while detecting said audible audio signal, and varying said external pressure until said audible audio response indicates that said diaphragm means is at said stop position, at which point the value of said external pressure is in said known pressure relationship to said internal bodily pressure to be measured.

5. The method of claim 4 wherein said means having a detectable characteristic response comprises said diaphragm means itself with said characteristic response being the generation of acoustic pressure waves in the bodily media surrounding said pressure sensor when said flexible diaphragm means moves, and wherein said external detection apparatus is adapted to detect said acoustic pressure waves and amplify them to produce audible acoustic signals, said flexible diaphragm means moving in a pulsatory motion and thereby producing pulsatory variations in said audible acoustic signals when the pressure sensor is implanted in the living body and the bodily pressure communicating with said first side of said flexible diaphragm means is pulsating with the cardiac pulsation rate, said method further comprising the step of detecting the point of diminution of the produced pulsatory acoustic signals as the external pressure is varied at which point said diaphragm means is at said stop position and the value of said external pressure is in said known relationship to said bodily pressure to be measured.

6. The method of claim 4 wherein said stop means and said flexible diaphragm means are so adapted that when said diaphragm means strikes said stop means at said stop position a sound wave is emitted with the emission of said sound wave being said characteristic response, and wherein said external detection apparatus is adapted to detect said sound wave and amplify it to an audible acoustic signal, and method further comprising the step of varying the externally applied pressure until said audible acoustic signal is detected and amplified to indicate that the diaphragm means has struck the stop means at which point the externally applied pressure is in said known relationship to said bodily pressure to be measured.

7. The method of claim 6 further comprising applying a variable pressure and a modulating pressure on the skin above the implanted sensor so that said variable pressure enables an average pressure to be communicated to said pressure sensor and to drive said flexible diaphragm means to said stop position while said modulating pressure modulates the movement of said flexible diaphragm means whereby when said flexible diaphragm means approaches said stop position said diaphragm means will strike said stop means in accordance with said modulated movement, and then varying the applied variable pressure until the audible acoustic signal indicates that the diaphragm means is striking said stop means in accordance with said modulating pressure, at which point the applied pressure is in said known pressure relationship to said bodily pressure to be measured.

8. The method of claim 6 wherein said external detection apparatus is a stethoscope, and further comprising the step of placing the stethoscope above the skin over the implanted sensor and listening for said sound wave.

9. The method of claim 4 wherein said means having a characteristic response is a resonant electronic circuit within said pressure sensor with said characteristic response being the resonant frequency of said electronic circuit, which changes with movement of the flexible diaphragm means, said method further comprising the steps of detecting said resonant frequency and converting the resonant frequency into an audible acoustic tone, the audio frequency of which is a function of said resonant frequency, and detecting the audio tone while varying said externally applied pressure until said audio tone ceases to vary with change of said externally applied pressure at which point said flexible diaphragm means has reached said stop position and the value of said externally applied pressure is in said known relation to said bodily pressure to be measured.

10. The method of claim 9 further comprising the steps of providing a reference audible signal having a reference audio tone and varying said acoustic tone so that the acoustic tone corresponding to said diaphragm means being in said stop position can be made equal to said reference audio tone, and varying said externally applied pressure until said acoustic tone equals said reference audio tone at which point the value of said externally applied pressure is in said known relation to said bodily pressure to be measured.

* * * * *

UNITED STATES PATENT AND TRADEMARK OFFICE
CERTIFICATE OF CORRECTION

PATENT NO. : 4,378,809
DATED : April 5, 1983
INVENTOR(S) : Eric R. Cosman

It is certified that error appears in the above-identified patent and that said Letters Patent is hereby corrected as shown below:

The portion of the term of this patent subsequent to June 10, 1997, has been disclaimed.

Signed and Sealed this

Thirty-first Day of May 1983

|SEAL|

Attest:

DONALD J. QUIGG

Attesting Officer    Acting Commissioner of Patents and Trademarks

UNITED STATES PATENT AND TRADEMARK OFFICE
CERTIFICATE OF CORRECTION

PATENT NO. : 4,378,809
DATED : April 5, 1983
INVENTOR(S) : ERIC R. COSMAN

It is certified that error appears in the above-identified patent and that said Letters Patent are hereby corrected as shown below:

Column 5, line 54, delete "descrete" and insert therefor --discrete--;

Column 6, line 4, delete "(EXP)" and insert therefor -- (EXT)--.

Signed and Sealed this

Twenty-second Day of May 1984

[SEAL]

Attest:

GERALD J. MOSSINGHOFF

Attesting Officer

Commissioner of Patents and Trademarks